(12) United States Patent
DeBenedetto

(10) Patent No.: US 10,244,759 B2
(45) Date of Patent: Apr. 2, 2019

(54) USE OF FORCHLORFENURON FOR PROMOTING PLANT GROWTH

(71) Applicant: KIM-C1 LLC, Fresno, CA (US)

(72) Inventor: Maury DeBenedetto, Fresno, CA (US)

(73) Assignee: KIM-C1, LLC, Fresno, CA (US)

( * ) Notice: Subject to any disclaimer, the term of this patent is extended or adjusted under 35 U.S.C. 154(b) by 0 days.

(21) Appl. No.: 14/509,759

(22) Filed: Oct. 8, 2014

(65) Prior Publication Data

US 2015/0099634 A1 Apr. 9, 2015

Related U.S. Application Data

(60) Provisional application No. 61/888,161, filed on Oct. 8, 2013.

(51) Int. Cl.
*A01N 47/36* (2006.01)
*A01N 25/02* (2006.01)

(52) U.S. Cl.
CPC ............. *A01N 47/36* (2013.01); *A01N 25/02* (2013.01)

(58) Field of Classification Search
CPC ......... A01N 47/36; A01N 25/00; A01N 25/02
USPC ....................................................... 504/210
See application file for complete search history.

(56) References Cited

U.S. PATENT DOCUMENTS

| 4,193,788 | A  | * | 3/1980  | Shudo et al. ................. 504/210 |
| 7,634,870 | B1 | * | 12/2009 | Burke ...................... A01G 7/06 47/5 |
| 2008/0318789 | A1 | * | 12/2008 | Fugiel et al. ................. 504/296 |
| 2010/0216641 | A1 | * | 8/2010  | Wang ..................... A01N 43/90 504/210 |

OTHER PUBLICATIONS

Hedin et al. , Plant Bioregulator Induced Increased in the Protein Content of Cotton Plant Tissues, 1988, Journal of Agricultural and Food Chemistry, vol. 36, pp. 742-745.*

Tang, R., Effects of Mixed Application of 4PU-30, Pix, and AVG on Increase of Cotton Boll Formation and Its Mechanism, 2001, Jiangsu Journal of Agricultural Sciences, vol. 17, No. 4, Abstract.*

* cited by examiner

*Primary Examiner* — John Pak
*Assistant Examiner* — Andriae M Holt
(74) *Attorney, Agent, or Firm* — Mintz, Levin, Cohn, Ferris, Glovsky and Popeo, P.C.

(57) ABSTRACT

A method is disclosed herein for promoting the root growth of a plant. The method includes contacting the plant, or a seed of the plant, with a composition containing forchlorfenuron (CPPU) before the reproductive growth stage of the plant, such that either the root length of the plant is at least about 5% greater than for an untreated plant, or the ratio of root length to stem length is increased by at least 5% compared to the untreated plant.

14 Claims, 3 Drawing Sheets

USE OF FORCHLORFENURON FOR PROMOTING PLANT GROWTH

CROSS-REFERENCE TO RELATED APPLICATIONS

This application claims priority to U.S. Provisional Application No. 61/888,161, filed Oct. 8, 2013, which is incorporated in its entirety herein for all purposes.

BACKGROUND OF THE INVENTION

Cytokinins are hormones that promote cell division and differentiation in plants. Most research into cytokinin biochemistry has focused on purine-derived cytokinins. These molecules are synthesized and metabolized naturally in plant tissue and target genes affecting the cell cycle and shoot meristem formation. Less understood are phenylurea-derived cytokinins, which can be synthesized in a laboratory and applied to plants exogenously. Since their discovery just over half a century ago, phenylurea-derived cytokinins have been shown to possess many of the same properties as purine-derived cytokinins, and have been used to promote plant growth in agriculture.

Forchlorfenuron (CPPU) is a phenylurea-derived cytokinin that has entered widespread use in the United States in the last ten years. Forchlorfenuron acts synergistically with natural auxins to promote lateral growth, and has been used to improve fruit size, fruit set, cluster weight and cold storage in grapes and kiwifruits. These growth enhancements have generally resulted from application of forchlorfenuron to plants at post-bloom growth stages, directly to flowers or developing fruit. There is scope to treat plants, particularly annuals and biennials, with forchlorfenuron at earlier growth stages and using different methods, and such treatments have the potential to affect growth more broadly. There is also a need for novel treatments that enhance root growth. Surprisingly, the present invention meets this and other needs.

BRIEF SUMMARY OF THE INVENTION

In some embodiments, the present invention provides methods of promoting root growth of a plant. The methods include contacting the plant, or a seed of the plant, with a composition containing forchlorfenuron (CPPU) before the reproductive growth stage of the plant, such that either the root length of the plant is at least about 5% greater than for an untreated plant, or the ratio of root length to stem length is increased by at least 5% compared to the untreated plant.

DETAILED DESCRIPTION OF THE INVENTION

Figure 1:
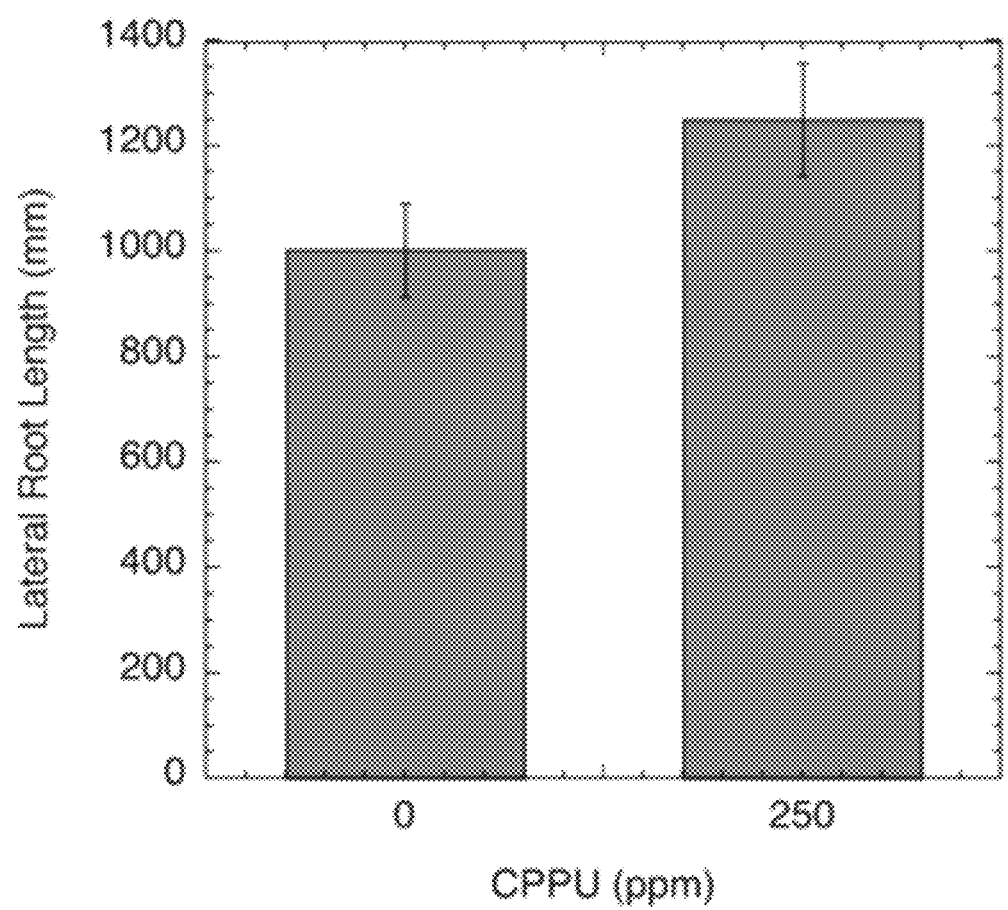
FIG. 1 shows increases in the lateral root lengths of cotton plants as a result of treating seeds of the plants with 250 ppm forchlorfenuron.

The inventors have surpisingly discovered that treating plants with forchlorfenuron before the reproductive growth stage can promote root growth. Treatment can involve contacting the plant, or a seed of the plant, with a composition containing forchlorfenuron at a concentration of 0.1-10,000 ppm. Treated plants, including broccoli and cotton plants, exhibit roots at least 5% longer than those of untreated plants, or root length to stem length ratios at least 5% greater than those of untreated plants.

I. DEFINITIONS

"Promoting root growth" refers to a method or process of increasing the length, thickness, number, maturity, weight, rate of growth, or depth of soil penetration of the roots of a plant, as compared with the roots of a plant not subjected to the method or process. A measurement of root growth for one plant can be compared directly with that of another plant, or can be compared after normalizing to a secondary measurement of the plant such as of stem growth. Promoting root growth can be achieved however desired by the practitioner, such as by contacting the plant with a chemical.

"Contacting" refers to bringing two or more objects or substances into physical contact. For example, contacting a first substance with a second substance may involve touching the two substances to each other, mixing the two substances together, burying or submerging one substance in the other, or passing one substance over or through the other. To contact one object or substance with another, the objects or substances may be brought together in any way feasible given their phases of matter and other material properties.

"Plant" refers to an organism that belongs to the kingdom Plantae.

"Seed" refers to the embryonic form of a plant, the structure surrounding or containing the embryonic form of the plant, or remnants of this structure. "Seed" is used herein without prejudice to whether the seed coat is intact or whether germination has begun.

"Forchlorfenuron" refers to the chemical compound having the molecular formula $C_{12}H_{10}ClN_3O$ and the CAS number 68157-60-8. "Forchlorfenuron" is used interchangeably herein with other names such as "CPPU", "4-CPPU", "1-(2-chloropyridin-4-yl)-3-phenylurea", "1-(2-chloro-4-pyridyl)-3-phenylurea", "N-(2-chloro-4-pyridinyl)-N'-phenylurea", and "N-(2-chloro-4-pyridyl)-N'-phenylurea", all of which refer to the same compound. Forchlorfenuron has the following structure:

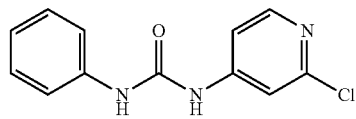 [SMILES: O=C(Nc1ccccc1)Nc1ccnc(Cl)c1]

"Growth stage" refers to the stage of growth or development of a plant. As desired, growth stage can be formally evaluated according to an established scale, such as the BBCH scale (Meier et al., *Journal für Kulturpflanzen* 2009) or the Zadoks scale (Zadoks et al., *Weed Research* 1974), or can be informally evaluated according to attributes such as the height of the plant or the presence of flowers. The "cotyledon growth stage" corresponds to growth stage 0 or 1 on the BBCH scale and is characterized by the cotyledons breaking through the soil surface and unfolding. The "six-leaf growth stage" occurs subsequent to the cotyledon growth stage, corresponds to growth stage 1 on the BBCH scale, and is characterized by the emergence and unfolding of the sixth true leaf. The "reproductive growth stage"

corresponds to growth stages 5-8 on the BBCH scale and is generally characterized by inflorescence emergence, flowering, and the development and ripening of fruit.

"Root length" refers to the length of the root or roots of a plant. Root length can be measured, calculated, inferred, or otherwise determined using any method or metric desired. For example, root length can represent the mean or median length of the roots of a plant; the length of the longest root; the length of the taproot; or the average or maximum depth of root penetration in the soil where the plant resides. Root length can also be normalized to another dimension of the plant, such as stem length. A skilled artisan will recognize that the length and disposition of a plant's roots change over the life of the plant, and any determination of root length reflects the age or growth stage of the plant at the time the determination is made.

"Stem length" refers to the length of the stem or stems of a plant. Stem length can be measured, calculated, inferred, or otherwise determined using any method or metric desired. For example, stem length can represent the length of the main stem; the average length of all stems; the average distance from the base of the plant to above-ground apical meristems; or the maximum height of the plant above the ground. A skilled artisan will recognize that a plant's stems grow over the life of the plant, and any determination of stem length reflects the age or growth stage of the plant at the time the determination is made.

"*Brassica*" refers to a genus of flowering plants in the Brassicaceae family. Species within the genus *Brassica* include but are not limited to *Brassica oleracea, Brassica rapa, Brassica napus*, and *Brassica carinata*. Herein, such species may be denoted "*B. oleracea*", etc.

"Broccoli" refers to the *Italica* cultivar group of the species *Brassica oleracea*, one or more varieties of broccoli (such as Calabrese broccoli or sprouting broccoli) belonging to this group, or one or more individual plants belonging to this group or varieties thereof. Broccoli can also refer to the portion of the plant harvested as food.

"*Gossypium*" refers to a genus of flowering plants in the Malvaceae family. Species within the genus *Gossypium* include but are not limited to *Gossypium hirsutum, Gossypium barbadense, Gossypium arboreum*, and *Gossypium herbaceum*. Herein, such species may be denoted "*G. hirsutum*", etc. Because *Gossypium* is known in the art as the cotton genus, "cotton" as used herein can refer to the entire *Gossypium* genus, one or more species belonging to this genus, or one or more individual plants belonging to a *Gossypium* species. "Cotton" can also refer to the crop harvested from a *Gossypium* species.

"Submerging" refers to holding an object within a composition for a sustained period of time. The object can be, for example, the seed of a plant. The composition can be a liquid, solid, gaseous stream, or any other form of matter, and can contain one or more chemicals that can react with the object. The period of time can be of any length, and can be selected as desired to effect a change in the composition or the object being submerged.

"Areal rate of application" or "rate" refers to the amount of a chemical, such as a nutrient or pesticide, applied to a cultivated crop over a certain area, and can be expressed in units of mass per area (e.g. grams/acre). Areal rate of application can represent the mean or median rate of application for a cultivated area, for example, and may not reflect variability in the amount of the chemical applied to individual plants within the area.

II. METHODS

Provided herein are methods of promoting root growth in a plant. The methods include contacting the plant, or a seed of the plant, with a composition containing forchlorfenuron (CPPU) before the reproductive growth stage of the plant, such that either the root length of the plant is at least about 5% greater than for an untreated plant, or the ratio of root length to stem length is increased by at least 5% compared to the untreated plant.

As defined above, promoting root growth involves causing the plant's roots to grow faster or more extensively than those of a plant not subjected to the method. Greater root growth allows the plant to gather water and nutrients in greater quantities, or in locations in the soil farther below the surface or farther from the base of the plant. Greater root growth also provides the plant with better anchoring in the soil and more mechanical support for the vertical and lateral growth of stems and branches. For these reasons, promoting root growth can lead to a larger, healthier plant and in turn a larger fruit or crop harvest.

The methods comprise contacting the plant, or a seed of the plant, with a composition comprising forchlorfenuron (CPPU), which belongs to a family of plant growth hormones called cytokinins (reviewed, for example, in Mok & Mok, *Annu. Rev. Plant Physiol. Plant Mol. Biol.* 2001, and in Sakakibara, *Annu. Rev. Plant Biol.* 2006). Cytokinins promote plant cell division (i.e. cytokinesis) and differentiation, among other processes, and are generally categorized as purine-derived or phenylurea-derived. Forchlorfenuron is phenylurea-derived. The compound is available from commercial sources (e.g. Sigma-Aldrich), is solid at room temperature, is weakly soluble in water, and is stable across a wide pH range. Forchlorfenuron has been shown to stimulate plant growth, for example increasing fruit size for grapes and kiwi fruit, although its molecular mechanisms of action are largely unknown. The inventors have surprisingly found that forchlorfenuron promotes root growth in agriculturally important plants such as cotton and broccoli.

In the methods provided herein, the plant is contacted with forchlorfenuron before the reproductive growth stage. As defined above, the reproductive growth stage corresponds to stages 5-8 on the BBCH scale and can be understood broadly to refer to the period when the plant flowers and produces fruit. A skilled artisan will recognize that many plants tolerate larger doses of chemicals (e.g. fertilizers or hormones) at earlier developmental stages, and the scope for further growth (and modulation thereof) diminishes as the plant matures.

According to methods of the invention, upon contacting the plant with forchlorfenuron, the root length of the plant is at least about 5% greater than for an untreated plant, or the ratio of root length to stem length is increased by at least 5% compared to the untreated plant. Treatment with forchlorfenuron can increase the sizes of various parts of the plant uniformly, or can cause some parts to grow more than others. Changes in the relative sizes of different parts of the plant upon treatment will vary with the species of the plant and the conditions under which the plant is grown, among other factors. Accordingly, in some cases (for example if forchlorfenuron causes roots to grow faster or more extensively than stems), a 5% increase in root length also corresponds to at least a 5% increase in the ratio of root length to stem length. In other cases, for example if forchlorfenuron differentially promotes stem growth, a 5% increase in root length corresponds to an even larger increase in stem length and a decrease in the ratio of root length to stem length. Under the definitions provided above, root length and stem length can be quantified as desired. Stem length can serve as a measure of the growth of the entire above-ground portion of the plant.

An untreated plant is a plant not contacted with forchlorfenuron. A skilled artisan will appreciate that comparisons between the root and/or stem lengths of treated and untreated plants are best made when other differences between the plants are eliminated or controlled for. For example, the treated and untreated plants should ideally be of the same species and growth stage, and should be grown under otherwise identical conditions. If desired, the untreated plant can be treated with a placebo, such as a composition lacking forchlorfenuron but otherwise the same as that with which treated plants are contacted.

In some embodiments of the invention, the plant undergoing treatment with forchlorfenuron is a member of the genus *Brassica* or *Gossypium*. Plants in these genera are angiosperms that typically grow in warm and temperate climates. These genera include plants of agricultural significance, such as green vegetables (*Brassica*) and cotton (*Gossypium*). Promoting root growth in *Brassica* or *Gossypium* plants has particular utility and economic value, because doing so can increase the yield of the crop portions of these plants.

In some embodiments, the plant can be a member of the genus *Brassica*. Plants in this genus are known as cruciferous vegetables, cabbages, or mustards, and grow worldwide endemically and by cultivation. *Brassica* species such as *B. oleracea, B. rapa, B. napus*, and *B. carinata* are grown as food, and different parts of the plant can be harvested. For example, turnips are the roots of *B. rapa*; rutabagas are the roots of *B. napus*; and mustard can be made from the seeds of *B. carinata*. *B. oleracea* alone has many phenotypically diverse cultivars corresponding to kohlrabi, cabbage, cauliflower, and broccoli, among other crops. Kohlrabi represents the stem of the *B. oleracea* plant, while cabbage represents the leaves and cauliflower and broccoli represent the flower heads. Accordingly, increasing the root length of a *Brassica* plant by treatment with forchlorfenuron can directly enlarge the harvested portion of the plant (e.g. turnips), or can feed the growth of parts of the plant that develop by the reproductive growth stage. Any member of the *Brassica* genus can be subjected to the methods provided herein.

*B. oleracea* is of particular interest because of the broad range of high-volume crops contained within this species. These crops include, in addition to those recited above, Brussels sprouts, kale, and collard greens. In some embodiments, the treated plant belongs to the species *Brassica oleracea*. *B. oleracea* cultivars typically grow biennially and have fleshy leaves. A subset of these cultivars is the *Italica* cultivar group, which corresponds to the crop broccoli and includes Calabrese broccoli, sprouting broccoli, and purple cauliflower. In some embodiments, the plant is broccoli. The harvested portions of a broccoli plant are typically the flowering head and the attached stem, which are rich in nutrients. The inventors surprisingly found that treating broccoli plants with forchlorfenuron at moderate concentrations increases the ratio of root length to stem length.

In other embodiments, the plant can be a member of the genus *Gossypium*. This genus comprises cotton plants, which are used to produce cotton fibers, oilseeds, and animal feed. *Gossypium* plants are generally shrubs that grow in arid tropical or subtropical climates. While the methods provided herein can be used to promote root growth in any *Gossypium* species, several species (*G. hirsutum, G. barbadense, G. arboreum*, and *G. herbaceum*) are of particular interest because together they represent over 90% of worldwide cotton production. In some embodiments, the plant can be a member of the species *G. hirsutum, G. barbadense, G. arboreum*, or *G. herbaceum*. The inventors found that treating *G. hirsutum* seeds or plants with forchlorfenuron increased lateral root development and increased the number of healthy cotton bolls per plant.

In addition to causing root length to increase, contacting a plant with the forchlorfenuron-containing composition can induce other kinds of growth or change in the plant. In some embodiments, for example, following the contacting step, the plant can exhibit reduced apical dominance, increased rate of development of fruiting branches, decreased time to first bloom, increased number of cotton squares formed, thickening of the hypocotyl, reduced rate of leaf wilting, reduced water usage, and increased root development, as compared to an untreated plant. When the plant is a cotton plant (i.e. member of the genus *Gossypium*), forchlorfenuron treatment can also cause the number of cotton squares formed to increase. These kinds of growth or change, and others known in the art, can be observed or measured using any methods desired. Such observations or measurements can be made any time after forchlorfenuron treatment, and involve any appropriate comparison between an untreated and treated plant.

A characteristic of particular interest that can correlate with root length or stem length is the weight of the plant or portions thereof. Plant weight can be measured as desired, such as by placing the plant or a portion thereof on a laboratory balance. Portions of a plant that can be weighed include the roots and stems, and these portions can be weighed at the same time that their lengths are measured. Other portions of the plant, including the seed from which it originates, seeds that it subsequently produces, shoots, or crop portions, can also be weighed, and weighing can generally occur at any time relative to the growth of the plant. In some embodiments, the plant is removed from the soil before weighing. In these embodiments, soil is preferably cleaned from the plant before weighing to improve the accuracy of the measurement. The plant can also be dried between removal from the soil and weighing in order to obtain a dry weight.

As discussed above, the plant can be contacted with the forchlorfenuron-containing composition at any time before the reproductive growth stage. For example, contacting can occur while the plant is still encased in the seed, just after the seed has germinated, or after the nascent plant has emerged from the soil. The timing of contacting can be adjusted as desired to maximize root growth, increase the ratio of root length to stem length, or achieve other growth outcomes. A person having ordinary skill in the art will recognize, however, that the timing of treatment needed to achieve a particular growth outcome can vary with the species or cultivar of the plant and growing conditions, among other factors. For example, in some cases, contacting a germinated plant with the composition can be effective to promote root growth when the plant is in the cotyledon or six-leaf growth stage, or between these stages. The cotyledon and six-leaf growth stages, defined above, correspond to the emergence and unfolding of the cotyledon(s) and the sixth true leaf, respectively. In some embodiments, contacting occurs at the growth stage of the plant from about the cotyledon growth stage to about the six-leaf growth stage. In some embodiments, contacting occurs when the plant is in the cotyledon growth stage. In other embodiments, contacting occurs when the plant is in the six-leaf growth stage.

As will be apparent to a skilled artisan, the amount of additional root growth achieved by administering the forchlorfenuron-containing composition to a plant depends on many factors, such as the species, health, and age of the plant, the growing conditions for the plant, and the details of the administration. The amount of additional growth also depends on how this growth is measured. Root length and stem length, as defined above, can be measured or quantified directly or indirectly, using any method desired. For example and without limitation, the root length of a treated or untreated plant can be determined by pulling the plant out of the ground and measuring the taproot or longest root with a ruler. Alternatively, average root length can be inferred from the weight or thickness of soil that clings to the plant when it is pulled out of the ground, or from the resistance of the plant to bending in the wind. Non-limiting examples of methods for determining stem length include measuring the height of the plant or the length of the main stem with a tape measure; measuring all stems and obtaining an average of these measurements; and determining the average distance from the base of the plant to above-ground apical meristems. Root length and stem length can be measured in tandem, by removing a plant from the soil, laying it horizontally, and measuring the lengths of portions of the plant that occurred below and above ground. Other methods of measuring root length and/or stem length will be apparent to those of skill in the art. In embodiments where these measurements are made after removing the plant from the soil, a certain amount of time can elapse between the removal and measuring to allow the plant to dry.

Root length and stem length can be quantified at any time during the life of the plant. Therefore, changes in root length, stem length, or the ratio of these variables due to forchlorfenuron can be observed at any time subsequent to treatment, including during or after the reproductive stage of the plant, even if these changes do not persist for the rest of the plant's life. Similarly, comparisons of root length or stem length between treated and untreated plants can be made any time after treatment, provided that the comparisons are properly controlled as discussed above. In such a comparison, the untreated plant need not be grown alongside or simultaneously with the treated plant, and the dimensions of the untreated plant at a particular growth stage can be obtained from a reference source, such as a journal article or trade publication, or simply be known in the art. In some cases, the same plant can serve as both the untreated plant and the treated plant for purposes of evaluating forchlorfenuron-induced root or stem growth. Here, the plant can be measured before and after forchlorfenuron treatment to obtain untreated and treated dimensions, respectively, and the plant should be in a sufficiently dormant state of growth that differences between these dimensions can be attributed to treatment rather than endogenous growth or senescence.

The amount by which the root length of the treated plant exceeds that of an untreated plant, under the particular methods of plant cultivation, forchlorfenuron administration, and growth measurement chosen by the practitioner, can vary widely. For example, as a percentage of the root length of the untreated plant, this amount can be 5%, 10%, 20%, or more. In some embodiments, upon contacting the plant, or a seed of the plant, with the composition, the root length of the plant can be at least about 5% greater than for an untreated plant. In some embodiments, the root length of the plant can be at least about 10% greater than for an untreated plant. In some embodiments, the root length of the plant can be at least about 20% greater than for an untreated plant.

Similarly, the ratio of root length to stem length can increase by variable amounts as a result of forchlorfenuron treatment. For example, depending on the parameters of treatment, the ratio for a treated plant can exceed that of an untreated plant by 5%, 10%, 20% or more. In some embodiments, the ratio of root length to stem length is increased by at least 5% compared to the untreated plant. In some embodiments, the ratio of root length to stem length is increased by at least 10% compared to the untreated plant. In some embodiments, the ratio of root length to stem length is increased by at least 20% compared to the untreated plant.

The forchlorfenuron-containing composition with which the plant is contacted can be prepared in any manner known in the art, have any consistency, and take any physical form. For example, the composition can employ a carrier, such as a solvent, as desired by the practitioner. Forchlorfenuron is a solid at room temperature and is poorly soluble in water, but can be dissolved in an organic solvent such as acetone, or in a mixture of such a solvent and water. Preferably, any carrier used is not detrimental to the health of the plant or seed. In some embodiments, the composition includes a solution, suspension, emulsion, or colloid.

The composition can be applied to the plant, or a seed of the plant, using any desired mechanism. If the composition is a solid (e.g. powder or pellets), it can be distributed on top of the ground where the seed has been planted or the plant is growing, or sown into the ground (i.e. inserted below the surface). If the composition is a liquid, it can be sprayed directly onto the plant, sprayed or dripped onto the ground, or infused into the irrigation system, for example. Other mechanisms of application are known in the art. The chosen mechanism of application can contact the entire plant or seed with the composition, or only parts of the plant, and this can be done selectively or not selectively. For example, a liquid composition containing forchlorfenuron can be sprayed over a plant such that substantially all above-ground parts of the plant are contacted uniformly, or sprayed without regard to what parts of the plant are contacted. Alternatively, the composition can be applied to selected parts of the plant, by spraying or by using a precision tool such as a paintbrush or eyedropper. In some embodiments, the composition is applied to the shoots, stem, cotyledons, or leaves of the plant, or to more than one of these parts. A skilled artisan will recognize that the mechanism of application, including the form of the composition and the parts of the plant contacted, can affect growth outcomes including root length.

Application can also occur by submerging or drenching a seed of the plant in the composition containing forchlorfenuron. Preferably, in these embodiments the composition has a consistency (e.g. liquid) that allows forchlorfenuron to readily diffuse into the seed. The practice of submerging a seed before planting, sometimes called 'priming', can be done as part of the methods disclosed herein at any age of the seed, at any point in the development of the seed (e.g. before or after germination), at any time before planting, and for any length of time. In some embodiments, the seed is submerged in the composition for from about 1 second to about 100 seconds. In some embodiments, the seed is submerged for about 10 seconds. As an alternative to submerging, the seed can be drenched by holding it in a permeable container, such as a screen basket, and pouring the composition over the seed while simultaneously allowing the composition to drain out of the container. Drenching may be preferable to submerging when the seed has a tendency to float or otherwise resist wetting. The duration of drenching can likewise occur at any time and for any length of time. In some embodiments, drenching is carried out approximately one week prior to planting and the treatment lasts about 10 seconds. As will be appreciated, submerging or drenching a seed in a composition for not enough time can have no significant effect on the growth of the plant emerging from the seed, and for excessive time can be detrimental to the growth of the plant. Following submerging or drenching and before planting, the seed can be dried or otherwise handled to remove excess forchlorfenuron or other components of the composition (e.g. water) to which it was exposed. Drying can also occur for any length of time, and any desired amount of time can elapse between the submerging or drenching and planting. The optimal timing of submerging or drenching and subsequent handling steps depends on the plant species, growing conditions, and other factors.

Any concentration of forchlorfenuron can be used in the compositions discussed herein. However, a person having ordinary skill in the art will recognize that a concentration should be chosen that is high enough to promote significant root growth, but not so high as to exert a toxic effect. The inventors found that concentrations ranging from 0.1 to 10,000 ppm met these criteria in various contexts. In some embodiments, the concentration of forchlorfenuron in the composition can be from about 0.1 to about 10,000 ppm.

The forchlorfenuron concentration needed to obtain the desired amount of growth, in the roots or other parts of the plant, depends on many factors, including the amount of the composition with which the seed or plant is contacted, the mechanism of application, the species and cultivar of the plant, the health of the plant, and growing conditions. Another such factor is the growth stage of the plant at the time of application. Plants generally tolerate lower doses of growth factors such as forchlorfenuron at later growth stages. Moreover, the inventors found that a lower dose was needed to promote roughly the same amount of root growth when the plant was in a later growth stage. Accordingly, a forchlorfenuron concentration in the range of about 1 to 100 ppm can be used in the composition when the plant is contacted at a relatively late growth stage, for example well after germination and just before the reproductive growth stages. In some embodiments, the concentration of forchlorfenuron in the composition can be from about 1 to about 100 ppm. In preferred embodiments, the concentration of forchlorfenuron in the composition can be from about 2 to about 25 ppm.

By contrast, at earlier growth stages, such as before or just after germination, higher concentrations of forchlorfenuron (e.g. 10 to 1,000 ppm) can be used. In some embodiments, the concentration of forchlorfenuron in the composition can be from about 10 to about 1,000 ppm. In preferred embodiments, the concentration of forchlorfenuron in the composition can be from about 25 to about 500 ppm. In more preferred embodiments, the concentration of forchlorfenuron in the composition can be about 250 ppm.

The amount of forchlorfenuron with which a plant or population of plants is contacted can also be expressed in terms of rate, i.e. the areal rate of application. As defined above, this is the amount of forchlorfenuron applied per unit area. The areal rate of application can be set as desired by the practitioner, in view of the number of plants that are being treated per unit area, among other considerations. If a plurality of plants (such as in a cultivated field) is contacted with the composition, equal amounts can be applied to each plant, or different amounts can be applied, at the same overall areal rate of application. Different amounts can be applied by accident, as a result of the mechanism of application, or intentionally, to reflect non-uniformity in the growth stages of individual plants, for example. A skilled artisan will recognize that a calculated or stated areal rate of application can represent the average rate for an area, and may not reflect variability in the amount of the composition applied to individual plants, groups of plants, or portions of the area. In some embodiments, contacting occurs at a rate of about 0.01 to about 100 grams forchlorfenuron per acre on average.

In some embodiments of the invention, a plant or seed can be contacted with the forchlorfenuron-containing composition at least twice. For example, the plant can be contacted prior to planting and then subsequent to planting, or before and after germination. To provide another example, an early application of forchlorfenuron can involve submerging a seed of the plant in a solution, while a later application can involve spraying the plant with the solution in the cotyledon stage or six-leaf stage. Any length of time (e.g., hours, days, or week) can elapse between consecutive treatments of the plant, and the timing of multiple treatments, amounts (e.g. mass, concentration) of forchlorfenuron in each treatment, mechanism of each treatment, and other parameters can be adjusted as desired. As discussed above, if desired, the amount or concentration of forchlorfenuron in the composition can be reduced between treatments as the plant matures, and later treatments can be applied more specifically to some parts of the plant.

In general, a treatment or contacting step as contemplated herein can take place over any amount of time. For example, treatment can occur as a brief event (spraying the plant in one pass) or over a prolonged period (exposing the plant to the composition through continuous irrigation). Therefore, multiple treatments can be achieved by removing the source of forchlorfenuron and then reinstating it, possibly in an altered form.

III. EXAMPLES

Example 1: Identifying Forchlorfenuron Seed Treatment Concentrations to Enhance Rooting in Cotton Commercial cotton seeds (*G. hirsutum*, FiberMax 9058, Bayer CropScience) were submerged in tubs containing forchlorfenuron at concentrations of 0, 25, 50, 100, 250, 500, 1000, 4000 and 8000 ppm for 10 seconds. The seeds were then placed on paper towels on the lab bench and allowed to air dry. Six days after the seed soak, the seeds were planted in "conetainers" and placed in a greenhouse for one week. The soil was removed from the conetainer and the roots were washed by gently dipping the soil into a bucket of water. Roots were photographed and evaluated for lateral root development. Initial tests revealed enhanced root production from 25 ppm to 1000 ppm with optimal lateral root production at 250 ppm. The test was repeated with eight plants per treatment, comparing 0 and 250 ppm forchlorfenuron, and clear differences in rooting patterns were observed (FIG. 1).

Example 2: Identifying Forchlorfenuron Seedling Treatment Concentrations to Enhance Rooting in Cotton Commercial cotton seed (*G. hirsutum*, FiberMax 9058, Bayer CropScience) was planted in conetainers and grown for 6 days prior to spraying with a range of forchlorfenuron concentrations. The plants were grown an additional 5 days prior to washing out the roots. Initial concentrations (0, 5, 10, 15, 20, 25, 50, 100, 250, 500, 1000, and 2000 ppm) were evaluated. Severe phytotoxicity was observed with forchlorfenuron applications above 50 ppm. Analysis of lateral root development revealed that the 5-ppm concentration exhibited the highest lateral root development of the treatments.

Example 3: Evaluating Cotton Yield Enhancement Under Abiotic and Biotic Stresses Cotton plants grown from commercial cotton seeds (*G. hirsutum*, FiberMax 9180 B2F, Bayer CropScience) were treated with forchlorfenuron at various stages of growth. Some seeds were treated with 250 ppm forchlorfenuron on Day 1, and all seeds were planted on Day 6. Some seedlings not previously treated were then sprayed at the cotyledon-first leaf stage with 5 ppm forchlorfenuron on Day 21. Some plants not previously treated were sprayed with 5 ppm forchlorfenuron at the 1st square stage on Day 41. Control plants were not treated at any stage of growth. At the time of harvest, cotton bolls on all plants were counted, and the percentages of bolls that were open and closed were calculated. These data are presented in Table 1.

TABLE 1

Evaluating cotton yield enhancement under abiotic and biotic stresses.

| | number bolls | % increase over control | % open bolls | % closed bolls |
|---|---|---|---|---|
| Control | 1080 | — | 39.8 | 60.2 |
| Seed soak | 1212 | 12 | 33.1 | 66.9 |
| Seedling spray | 1202 | 11 | 29.5 | 70.5 |
| $1^{st}$ square spray | 1096 | 1 | 43.3 | 56.7 |

Figure 2:
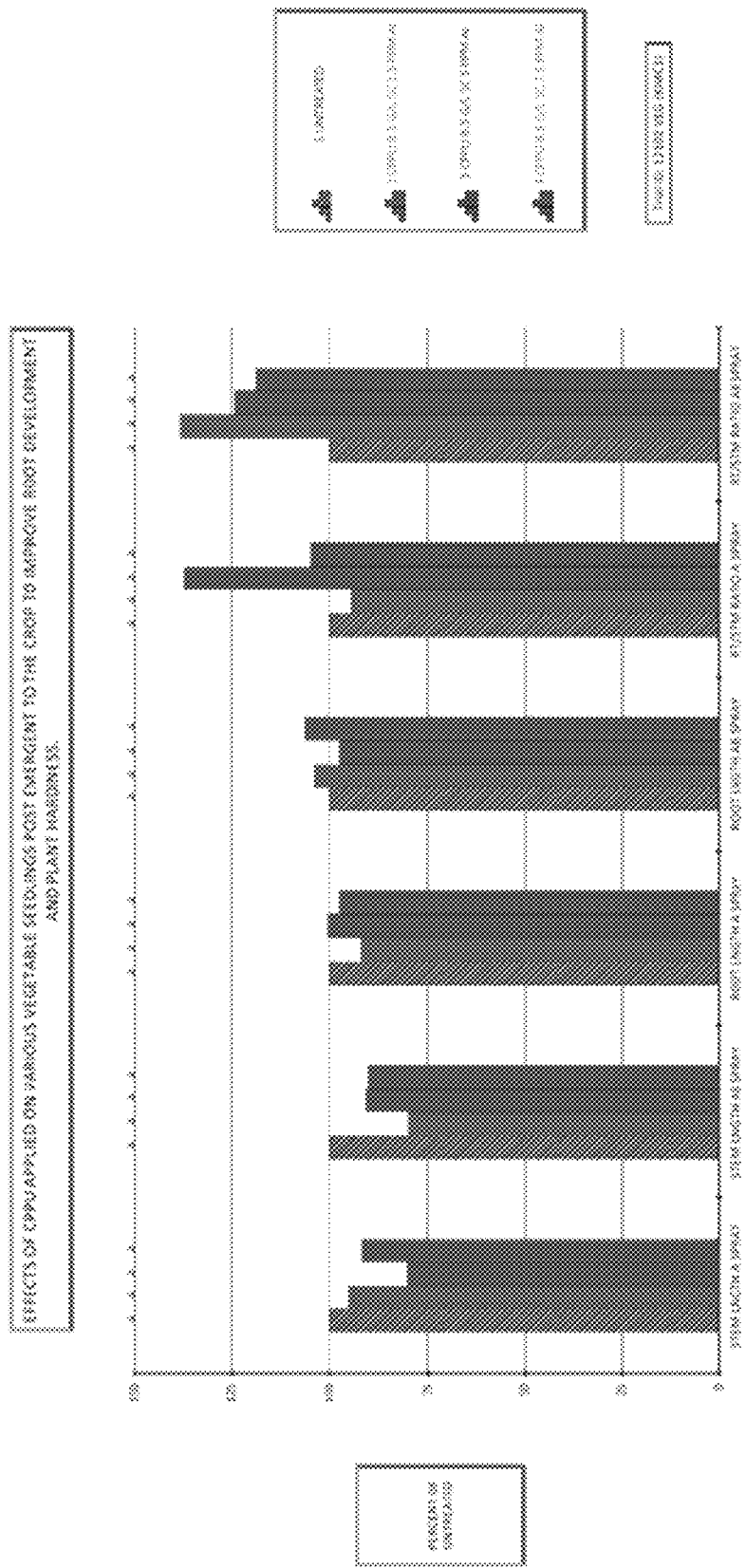
FIG. 2 shows changes in the root length, stem length, and ratio thereof for broccoli plants as a result of treating plants in the cotyledon growth stage with forchlorfenuron.

Example 4: Effects of Forchlorfenuron Concentration on Broccoli Root Length, Stem Length, and the Ratio Thereof Broccoli plants (*B. oleracea*, var. Waltham 29) were sprayed with 0, 2.5, 5, or 7.5 ppm forchlorfenuron at the cotyledon stage of growth (treatment A) and optionally again with 5 ppm forchlorfenuron three days thereafter (treatment B). The root length and stem length were measured 60 days after planting and the ratio of root length to stem length was calculated for every plant. Treatment A alone at 5 ppm resulted in a >20% increase in the ratio of root length to stem length above the untreated level, as did treatment A at 2.5 and 5 ppm together with treatment B. Results are shown in FIG. 2 and Table 2.

TABLE 2

Effects of forchlorfenuron concentration on broccoli root length, stem length, and the ratio thereof, as percentages of the untreated levels.

| Trt No. | Treatment Name | Rate | Rate Unit | Appl Timing | Shoot Length A Spray | Shoot Length AB Spray | Root Length A Spray | Root Length AB Spray | Root/Shoot Ratio A Spray | Root/Stem Ratio AB Spray |
|---|---|---|---|---|---|---|---|---|---|---|
| 1 | UNTREATED | | | | 100 a[1] | 100 a | 100 a | 100 a | 100 a | 100 a |
| 2 | CPPU | 2.5 | ppm ai | AB[2] | 95.25 a | 79.98 a | 91.86 a | 104.39 a | 94.53 a | 138.67 a |
| 3 | CPPU | 5 | ppm ai | AB | 80.12 a | 90.62 a | 100.6 a | 97.39 a | 137.48 a | 124.29 a |
| 4 | CPPU | 7.5 | ppm ai | AB | 91.78 a | 90.13 a | 97.46 a | 106.69 a | 105.16 a | 119.08 a |
| | Treatment F | | | | 2.418 NS[3] | 1.214 NS | 0.208 NS | 0.249 NS | 2.138 NS | 0.959 NS |
| | Treatment Prob (F) | | | | 0.1335 | 0.3595 | 0.8885 | 0.8603 | 0.1654 | 0.4531 |

[1]Means followed by the same letter are not significantly different by Duncan's New Multiple Range Test at p = 0.05.
[2]Spray application A = cotyledon stage. B = 3 Days after A application with 5 ppm CPPU.
[3]NS = Not significant at p = 0.05.
* denotes statistical significance and a single * was least significant.

Figure 3:
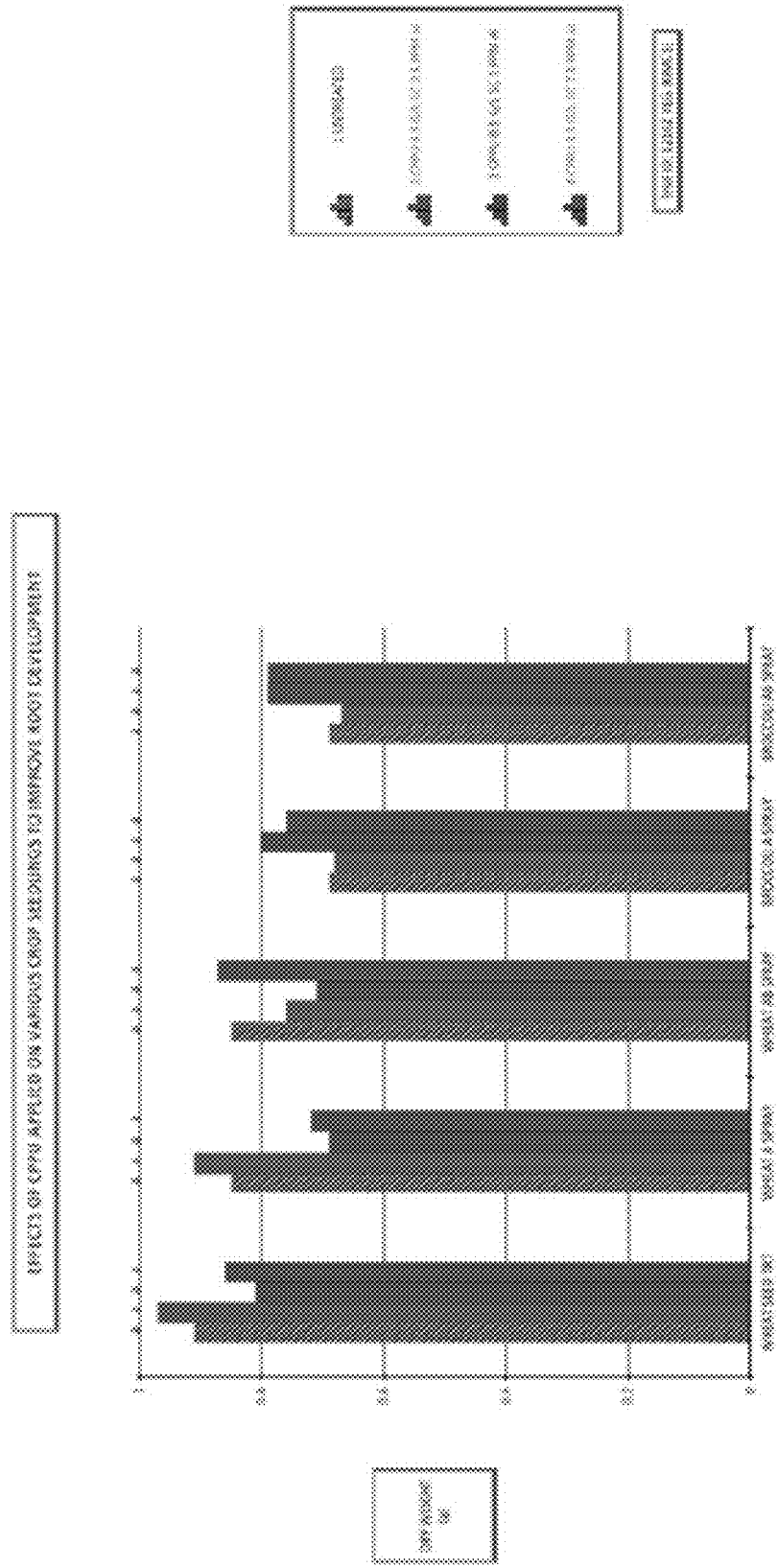
FIG. 3 shows changes in the dry weights of roots for wheat and broccoli plants as a result of treating plants in early growth stages with forchlorfenuron.

Example 5: Effects of Forchlorfenuron Concentration on Wheat and Broccoli Root Weight Plants were sprayed with 0, 2.5, 5, or 7.5 ppm forchlorfenuron, at the cotyledon growth stage in the case of broccoli or at stage 1 in the case of wheat (treatment A), and optionally again with 5 ppm forchlorfenuron three days thereafter (treatment B). The dry weights of the plant roots were measured 50 days after planting. For broccoli, treatment A at 5 or 7.5 ppm in the presence and absence of treatment B resulted in a >10% increase in root weight above the untreated level. Results are shown in FIG. 3 and Table 3.

TABLE 3

Effects of forchlorfenuron concentration on wheat and broccoli root weight. Weights are expressed in grams.

| Trt No. | Treatment Name | Rate | Rate Unit | Appl Timing | Winter Wheat Seed Treat. | Winter wheat (A spray) | Winter wheat (AB spray) | Broccoli (A spray) | Broccoli (AB spray) |
|---|---|---|---|---|---|---|---|---|---|
| 1 | UNTREATED | | | | 0.91 a[1] | 0.85 a | 0.85 a | 0.69 a | 0.69 a |
| 2 | CPPU | 2.5 | ppm ai | AB[2] | 0.97 a | 0.91 a | 0.76 a | 0.68 a | 0.67 a |
| 3 | CPPU | 5 | ppm ai | AB | 0.81 a | 0.69 a | 0.71 a | 0.8 a | 0.79 a |
| 4 | CPPU | 7.5 | ppm ai | AB | 0.86 a | 0.72 a | 0.87 a | 0.76 a | 0.79 a |
| | Treatment F | | | | 0.519 NS[3] | 1.277 NS | 1.094 NS | 0.869 NS | 1.09 NS |
| | Treatment Prob (F) | | | | 0.6795 | 0.3399 | 0.4005 | 0.4921 | 0.4021 |

[1]Means followed by the same letter are not significantly different by Duncan's New Multiple Range Test at p = 0.05.
[2]Spray application A = stage 1 (wheat) or cotyledon stage. B = 3 Days after A application with 5 ppm CPPU.
[3]NS = Not significant at p = 0.05.
* denotes statistical significance and a single * was least significant.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of promoting root growth of a plant, the method comprising contacting the plant, or a seed of the plant, with a composition comprising forchlorfenuron (CPPU) before the reproductive growth stage of the plant, such that either the root length of the plant is at least 5% greater than for an untreated plant, or the ratio of root length to stem length is increased by at least 5% compared to the untreated plant, wherein the plant is a member of the genus *Gossypium*, wherein the concentration of CPPU in the composition is from about 2 to about 50 ppm when the plant is contacted, and wherein the concentration of CPPU in the composition, is from about 25 to about 1000 ppm in the composition when the seed is contacted.

2. The method of claim 1, wherein the plant is a member of a species selected from the group consisting of *Gossypium hirsutum*, *Gossypium barbadense*, *Gossypium arboreum*, and *Gossypium herbaceum*.

3. The method of claim 1, wherein following the contacting step, the plant exhibits at least one characteristic selected from the group consisting of reduced apical dominance, increased rate of development of fruiting branches, decreased time to first bloom, increased number of cotton squares formed, thickening of the hypocotyl, reduced rate of leaf wilting, reduced water usage, and increased root development, as compared to the untreated plant.

4. The method of claim 1, wherein the contacting occurs at the growth stage of the plant from about the cotyledon growth stage to about the six-leaf growth stage.

5. The method of claim 4, wherein the contacting occurs when the plant is in the cotyledon growth stage.

6. The method of claim 4, wherein the contacting occurs when the plant is in the six-leaf growth stage.

7. The method of claim 1, wherein the root length of the plant is at least 5% greater than for the untreated plant.

8. The method of claim 1, wherein the root length of the plant is at least 20% greater than for the untreated plant.

9. The method of claim 1, wherein the ratio of root length to stem length is increased by at least 5% compared to the untreated plant.

10. The method of claim 1, wherein the ratio of root length to stem length is increased by at least 20% compared to the untreated plant.

11. The method of claim 1, wherein the composition is applied to at least one member selected from the group consisting of the shoots, stem, cotyledons, and leaves of the plant.

12. The method of claim 1, wherein the seed is submerged in the composition for from about 1 second to about 100 seconds.

13. The method of claim 1, wherein the concentration of CPPU in the composition is from about 2 to about 25 ppm when the plant is contacted.

14. The method of claim 1, wherein the concentration of CPPU in the composition is from about 25 to about 500 ppm when the seed is contacted.

* * * * *